(12) United States Patent
Khosla et al.

(10) Patent No.: US 6,340,774 B1
(45) Date of Patent: Jan. 22, 2002

(54) NON-STEROIDAL ESTROGEN-RECEPTOR ANTAGONISTS

(75) Inventors: Chaitan Khosla, Palo Alto; Zhihao Hu; Thomas Marti, both of Stanford, all of CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/773,816

(22) Filed: Jan. 31, 2001

Related U.S. Application Data

(60) Provisional application No. 60/243,458, filed on Oct. 25, 2000, and provisional application No. 60/179,305, filed on Jan. 31, 2000.

(51) Int. Cl.[7] ..................... C07C 49/115; C07C 49/215; C07C 49/796
(52) U.S. Cl. .................. 568/326; 568/329; 568/373
(58) Field of Search ................. 568/326, 329, 568/373

(56) References Cited

U.S. PATENT DOCUMENTS 4,188,495 A * 2/1980 Althuis et al.
5,480,913 A * 1/1996 Liao et al.

OTHER PUBLICATIONS

Black et al., J. Clin. Invest. (1994) 93:63–69.
Hori et al., The Journal of Antibiotics (1993) 46(7):1055–1062.
Love et al., New England Journal of Medicine (1992) 26:852–856.
Katzenellenbogen and Katzenellenbogen, Chem. Biol. (1996) 3:529–536.
Kedar et al., Lancet (1994) 28:1318–1321.
Mosselman et al., FEBS Letters (1996) 392:49–53.
Paech et al., Science (1997) 277:1508–1510.

* cited by examiner

Primary Examiner—Johann Richter
Assistant Examiner—Sikarl A. Witherspoon
(74) Attorney, Agent, or Firm—Morrison & Foerster LLP

(57) ABSTRACT

This invention relates generally to non-steroidal estrogen-receptor (ER) antagonists that are useful as therapeutics in the treatment of advanced stage breast cancer. More particularly, this invention relates to the cloning and heterologous expression of genes encoding ER antagonists. This invention also relates to the use of such expression to overproduce the ER antagonist and analogs thereof.

1 Claim, 4 Drawing Sheets

HU235

SEQUENCE LISTING

<160> NUMBER OF SEQ ID NOS: 1

<210> SEQ ID NO 1
<211> LENGTH: 23673
<212> TYPE: DNA
<213> ORGANISM: Human
<220> FEATURE:
<221> NAME/KEY: misc_feature
<222> LOCATION: (1)...(23623)
<223> OTHER INFORMATION: n = A,T,C or G

<400> SEQUENCE: 1

```
ccaccggggc tcgtccccgt gccgcaccgg gtcggttgtt cgtgtcgcgt cgccctgcga      60
cgacgcggca gtcactccgt gcggcggcaa accgggtttc acacgtcggt ggttcgcacc     120
gacgggcgtg ctcccggtcg tgggtcgagc ccggccgggc gtcgggcggc ggcggttcgc     180
gccgtcgtcc gtcgctccgg ccacgccggc ctcccccgtt gccgcgcgga tgcgcgacga     240
cgggaggccg gccagggtcc cggcggcggt ggttcgcacc gtcgcccggc cctccgagat     300
cgaggtcccg gtggtcgtgg gccgccgacg tgcgccgcgc ggtcgcgtcg ggtcgcatgt     360
cggtcggctc ggcttctaca gttcgggggtt catcgcgcgg accacgacgg ccgcgttgaa     420
cccgccgtgg ccgcgggcca gcaccagcac cgtccgcacg cgcgcgttgc gcggttcgga     480
```

-continued

| | | | |
|---|---|---|---|
| cagcacgagg | tcgagcccgt agtcggccgg cacgtcggtg gtgttgggcg tcggcgggac | 540 |
| gacgtcgtcg | cggatcgaca acagcgcggc caccacgtcg agcggcggcc cgcccgagtt | 600 |
| gaggcgtccc | accaggctct tgggcgccgt caccggcacc cgccggccc cgaacacctc | 660 |
| gttgatcgcc | tcggcttcgg cgcggtccag gtccggtacg ccggccgcgt ccgcgaacac | 720 |
| cgcgtccacg | tcctcgggcc gcacgcccgc gtcgtcgagc gcgaggcggg ccgcgcgggc | 780 |
| cagccccggc | ggccgttcgg agccgggcgg cgggtcgaag gtggccgcgt agcctgcgat | 840 |
| ctcgccgtag | agcgtggccg cgccccgggc ccgggcggcg cgttcgtcct ccaggacgag | 900 |
| gatggccccg | ccctcccccg gcacgtagcc gtcggcggcc gcgtcgaacg gccggtaggc | 960 |
| cagctcgggt | tcggtcgcgc gggagatccg tccggtggtc aggtggctga cgtatcccca | 1020 |
| cgggtcgagc | gccgagtcgc atccgccggt gaccacgagg tcgatgccgc ccgcaggtt | 1080 |
| gcggcgcgcg | tggccgatgg cgtcgaggcc gccggcttgt tcgccgacca ggacgccgct | 1140 |
| gggcccgcgc | atgccgtgcc ggatggacaa ctggccggtg ttgacggcgt agaaccacgc | 1200 |
| gaacgactcg | tagacgctga cgtgttgcgc tcccttggtc cagagcttgt gtacctcgcc | 1260 |
| gtgggtgaac | tcgaagccgc cgatggcgct ggaggtgacg acgcccatcg agtagtcgac | 1320 |
| gagtgcctgc | gggtcgacgc cggcgtcgtc gagcgcgctc tggccggcga cgagggcgag | 1380 |
| tcgcgtgacg | cggtcggtct gcggcaacag ccttcccgga atgtgctgtt cggcctcgaa | 1440 |
| gccgagtatc | tggccggcga tcgggacgg gaatccggac gcgtcgtagc ggtgcagcgg | 1500 |
| gtggatgccg | gagcgtccgc gcagcgtggc cttccagtac tcctcggtgc cgaagccgtt | 1560 |
| gggggcaacg | gcgccgaggc cggtgacgac ggcgcgccgc gtcgtggggg ctgcctgggt | 1620 |
| catcgcgcgt | cctcctgaag gcggcgcagc accatcgcgc tctggaagcc accgaagccg | 1680 |
| ctgccgaccg | acagcacggt gtcggtgcgg tgttcgcggg cggtcaccgg cacgtagtcc | 1740 |
| aggtcgcatt | cggggtcgga ctgggtcagg ttcgcggtcg cggcacgac gttgtgctgg | 1800 |
| atcgcgagga | cgctggcggc gatctcgatg gagccgatcg cgccgagcga gtgcccgatc | 1860 |
| atcgacttga | tggagctgac cgggacgtcg taggcgtggt cgccgagggc gaccttgaac | 1920 |
| gcgttggtct | cgtgccggtc gttctgcttg gtcccggacc cgtgggcgtt gatgtagtcc | 1980 |
| accgccgtcg | gtcgatgcg cgattcgttc agcgcgtagg tgatggcgtc ggccatctcc | 2040 |
| cgtccgtcgg | ccttgagtcc ggtcatgtgg tacgcgttgc agcgggtcgc gtagccggtg | 2100 |
| acctcggcgt | agatgtgcgc gccgcgcgcc ttggcgtgct cgtactcctc gaggacgaac | 2160 |
| atcgccgccc | cctcgccgat cacgaatccg ctgcgggtca ggtcgaacgg cctcgacgcg | 2220 |
| gactcgggtt | cgtcgttgcg cggggtggtg gccttgatgg cgtcgaagca cgcgacggcg | 2280 |
| atcggcgaga | tcggcgcgtc ggtggcgccg gtgaccatga tgtcggcggt gccctcgacg | 2340 |
| atgagctggt | aggcgtagcc gaccgagtcc aggcccgagg tgcagccgga ggacacgatg | 2400 |
| gtcgcggggc | cctccgcgcc gacgctccag gccacttcgg cggcgatcgc gccgggcgtg | 2460 |
| aagtagtcgt | acatgtgcgg cgtggcgtag tcggcgtcga ccacccagtc gcgtccggag | 2520 |
| tcggagagca | cgaggtattc gcgttcgagg ctcgtggtgg cgccgacggc gctgccgacg | 2580 |
| ctgactccga | tccgggtcgg gtcgaggtcg gcgaacgcca gtccgctgtc ggcggcgcag | 2640 |
| tcccgcgcgc | tggcgacggc gaacagcgac gcgcggtcca ggcggcggat ctcgcggtgc | 2700 |
| gtgaagccgg | ccaggaccgg gtcgaagtcg cattccgcgg ccacctggga ccggaacggc | 2760 |
| gacgggtcga | agtgggagat cgccgggtg gcggtgcggc tgaggtgag caggtcccag | 2820 |
| aaccccttgg | ttccggtgcc gcccgggcc acgaccccca tcccggtgat caccgctcgt | 2880 |

-continued

```
cgttccaaga caagcctcca gcggtggtgt cggttgttgc tgtgctcttc gagcgtgcgt      2940
ggcgcgactc gaaccgtgct caaggacgga tcgcgcggag tcgcgggccg ttgtcgagtg      3000
ggggtcgagt ggcgtgcgcg agcctcgtgg acccctgtag atgtactcgg gtcgaggaga      3060
cctccgatga cgatcagact ggttccgccg cgccgccgtg tcgccctgct gctgccgggg      3120
cagggctcgc aacaccccgg tatggggctg gagttgtacg gctacgacgg tgtgttcacc      3180
gagacgatgg acgagatgtt cgagctgctc gggccggtgg acggcgcgtc gctgcgcgcc      3240
gactggctgc ccggcgacgc gctcgcgccg gagctgctga cgacgcgag ccgcgcgcag       3300 ccgctgttgt tcgcggtcga gtacgcgctg ggccgcagcc tgttgtcgca gggcgtcgac      3360
gtggacgtgc tgctcgggca cagcgtcggc gagttgtcgg cggcggcgtt ggccggcgtc      3420
gtcgacctgc cgggcgcggc gcgcgtgatg gcggcccgga ccgcggcgtt ggccgcgctt      3480
cccccgggcg ggatgctcgc ggtcgcgcg accgccgagg agttggcgcc gttcgtggcc       3540
gccgagcacg tcgagatcgg cgtggtggtg ggcgcgttga acgcgccgcg gcagaccgta      3600
ctggcggggc ccgagccgcg gttgaccgag gtggagggcg aactgcgggc ggccggtgtg      3660
atgttccgtc gggtgccggc gcggcagccg ttccactccc ccgcgtcggc gccggccgcc      3720
gaggtggtgg agaaggtgtt gtccggggtg acgttgcgcg agccgacgat cccgatcatg      3780
tcgacgcact cgggcgccta cgtgacccgc gagcaggccc tcgacccggc cttctgggcc      3840
tggcacttcg tgcgcgtggt gttgttctgg ccggcgttgg acgcgctgct ctccgaggcc      3900
gaccacgcgc tcgtcgagct gggcccgggc caggagctga cggtgctggc gcgccggcac      3960
aaggcggtcc ggtcgggcgc cagcacggtg cgcgcggtgt tgccgcgcgg ggcgcgcggt      4020
acgcgggagg cgtgggacga cgcgctggcc gaactggccg agtacaccgg gccggccggg      4080
ggtgtgccgc tcgcctgcgc ggcggaacgg tgaacgtggc actccgccgc gggcggcgcc      4140
gccaacgccc ttgagaagcc cggaccgtgg cggtggtccc gtgtcctcgt caccttccgg      4200
tgggcgacgt cgcctcctac attggcgggt aaggcggcga ggacatggag gctcggatga      4260
gcggtgcctg ggtgcgcagt gccgacggac tctcgttgat ccgcgcggtg gagatcgtct      4320
ccctgagggt caacggcacc gccctcgaat gcgactcgcg cctggcccgc gccttcgtcc      4380
tggccaccgg cgccgaggag gatctggtcc ggggcgcacg ggagttgatc gagacgctgg      4440
cccgactgcc gcacgacgcc tacatcgtct cggccgatgt gaccgacggg cgtgtcgtgt      4500
gggcgctctc cgagatcggc ccggtcgagg acgacccgcc gtacgccgcg ggcgggcagg      4560 cttacgggggc gaccgccag gtgtacggcg cgggcatgcc cggtaggccg atgccggggga     4620 tgccgatggg gggcgcgtgg ccgccctggg gcaacccgcc gccgcacagg tgagcctcgg      4680
gtccggcaca tcccgttccg ggcccggccc ccgcctcgcg gtacgcgaac accccgccc       4740 ggcccgcggc gtcgtcgttc gcgggccggg cggaggcggg ggtcggcgtg cctgggagca      4800
ccgccgggca cgccgaccgc ttcacgcgga cagggcact cccgtccgcg cgttccgggc       4860
ctcggcggcc agcatctcgt cgacgaggga ggtgctgtgg cgtccggcgg cgaacttgtc      4920
gttgtcgaac acctcgcgca ggaacccgat ggtggtgcgc accgttggc cctcgacctc       4980 gaactggtcg agcgcgcggc gcatgcgggc gagggcctgt tcgcggtccg gtgcccacac      5040
cacgagcttg gccagcagcg agtcgtacga cgcgggcacg gtgtacccgg cgtgcacgtg      5100
tgtgtcgacg cgcacgaacg ggccgccggc gggcgtgaac gtgtcgatca gccctggcgt      5160
cggcacgaat ccgcgcgtcg ggtcctcggc gttgatgcgg cactccatgg acacgccgtt      5220
```

-continued

```
gggtcggatg tcttcctggc gcaccgtcag cggacggccg gcggcgacca ggatctgctc    5280
gcgcaccagg tcgatgccgg tgaccatctc tgtgaccggg tgctcgacct ggatacggca    5340
gttgacctcc atgaaggaga acgttccgtc gggcgcgagc aggaactcga acgtgccggc    5400
gccgacgtag ccgaccgcgc gcgccccggc gacgccgcc tcgcccatcc gggcggcgag    5460
gccgtccgga agccggggcc cggcgtctc ctcgacgagc ttctggtgcc ggcgctgcac    5520
ggagcagtcg cgttcgccca ggtggacgac gttgccgtag cggtcggcga gcacctggat    5580
ctcgacgtgc cgggcctcgg gcaggtagcg ctcgacgtac accgcccgt cgccgaacac    5640 cgccaacgcg gtggcctggg tgcggcggaa cgtgtcgggg aagtcgtcgc tggagtggac    5700
caccgacatg ccgcgcccgc cgccgccggc cgccgccttg acgatgacgg ggtagccgat    5760
cgtgtcggcg agcgcgtgcg cctcgcggtc ggagagcggg tcgaggctgc cgggcagcag    5820
cggaaggccg gcctgcgaca tgatcgaccg ggcggacgcc ttgttcccga ccgcgacat    5880 cacctcggcg ggcgggccga tgagggtgat gccctcgtcc tcgcacgcct cggcgaagtc    5940
cgggtcctcg gacaggaatc cgtagccggg gtggaccgcc tcgacgccgg tctgcacggc    6000
ggcctggagc acggcggcgg cgttgaggta gctggcgcgc ggcggggcgg ggccgacgca    6060 cacgcctcg tccgcgaacc gcacggcggc ggagtggcgg tcggcatcgg agtgcacgac    6120
gacggtccgg atgccgagct cccgacaggt cgcggcgaca cgcagcgcga tctcgccgcg    6180
gttggcgatg agtaccttct cgaacatgtc gggctacgcg ccttccacgg ggaccagcgc    6240
gacgagcggc tcgccgtact cgacctggtc gccgttggcg cgcaggatcg cggacacccg    6300
gccgggacgg tcggcctcga cggggagcat gagcttcatc gcctcgacga tgccgatctg    6360
ttgaccgggg cggaccacgt cgccgacccg cacgaacggc gcggcgccgg gctcggtggc    6420
gtggtagaac acgccgacgc tgggcgcgca cacctggtgc gcggtcggct ccgccggggg    6480
cgcgggcacg ggcggcggcg cggcgacggc gggcacggtg cgacgggaa cggcggacac    6540 gacgggctgg ggcaccgccg gggcctgcgg cgcctcccag gacacctcga tcccgacgcc    6600
gtccgcgcgc acgttgagcc gcgtgggccg ctcgggcaac gcttcgagca tctcgatgac    6660
ggagtgccgc agggtgttca caaccgcgc ggcgtcctcg tcggcgccct cgccgccgcg    6720
taccgcgggg tcggcgatcg gggtgatggt cacggtgtct ccttctcctt gattcctgta    6780
cgtctacgcg gccgcgccac ggacggcccc tcgggacaca ccacctgcgc ggccgccccg    6840
accccgtgcg cgagcgccac ggcgagcccg cccgagagca cgagccgaaa cccgaccccg    6900
accacacccg cgacggtcga cggggagtcc tcccccggcc gcacgtggtg ggcgcgaagc    6960
aacgcccgcg aaacgggctg aacggcttcg acgaggggct gaggcgtcat gccgtcacca    7020 cacgcgcg ggtcgcgcgc accaggccga agcagcgagg cggcggggcc gcggatgcga    7080
ggacgccgct gggcgacgcg gcgactcgag gcaccgacac cccgccgtca cccccacaac    7140
cgccgcgcgc agcgccggtg ggtctcacgt cgggtcgcct ttcatggcgg tgatctcggc    7200
gtcggtggtg cgttccgcgc catagcggcg gaagcgggcc cagcggtcgg cgaccaactg    7260
gtggccgtcg agggggaca actccgcgag gccgccgcg atcgcgtcgc ggagggcgtc    7320 ggcgcgcgc agcgggtcgg ctccggtgcc gccttcgggt tccggagga cgccgtcgac    7380 gatgcccagg ccgaggagtt cgcgggcggt gaccctcagc gcgcgggcgg cacgcccggc    7440
ggcggcgggg tcctgccaca ggatggccgc gcagccctcg gggctgatga ccagtagat    7500 gccgttctcg aacatcagga cacggttggc gacggcgagc gcgagcgccc cgccgctgcc    7560
gccctcgccg gtgacgacgg tgacgaccgg cacgcgcagg cccgccatca ggcgcaggtt    7620
```

-continued

```
ctcggcgatg gcgacggcct ggccctgctc ctcggcgacc gcgccggggt aagcgccggg      7680
ggtgtcgacg aacgtgacga ccgggagacc gagtttgtcg gcgagccgca tgatccgggc      7740
ggccttgcgg tagcccgacg ggatcggcat gccgaagttg cggcggcgca gctcctgcgc      7800
gtcgtggccc ttctggtggc cgatgacggc gacgggtcgg ccgccgaagc gggccaggcc      7860
ggcgacgatg gcggggcagt cgcccgagat gcggtcgccg cgcagttcga cgaagtcctc      7920
gcacagcagc gcgatgtagt cgagcgtggt gggccggtcg atggcccgcg cggcgcgcac      7980
ctggcggctg ggtcgtgcg cggcgaggtc ggcggggtcg acgacgtacg gcgatgcccc       8040
cgcgtccagg ccgccgcgtc gggccggttc ccgtccccg cccttgggcc gcttcgcgcc       8100
ggcccgcagc aggcgggcca gttcgtcgcg cagcgcgcgg cgcggcacga tcaggtcgat      8160
caggccgtgt tcgaggaggt attcggcggt ctggaactcc ggcggcagtt cctcgcggat      8220
ggtctgcgcg atgacccgcc ggccggcgaa gccgagacgc gcgccgggtt cggcgacgat     8280
gacgtcgcac agggtcgcga aggacgccgc gacgccgccg taggtggggt cggtgaccag      8340
cgagatggtc aacacgccgg cctcgtccag ttgcccgagg gcggcgctgg tcttggccat      8400
ctgcatgagc gcgacggcgc cttcctgcat gcgcgcgccg ccggacgcgc tgacgatcag      8460
cagcggcagg tgttcggcga gcgcggtctc ggcggcgagg gtgatcagtt cgccgaccgc     8520
gccgcccagg ctgccgccga ggaacgcgaa gtccatcgcg gcgacgacga gcggctggcc     8580
gtggatccgg ccggtcacga tgacgacggc ctcgtcgagc ccggtggcgg cacgcgcggc     8640
ggcgagccgc gcggggtagg gcttggtgtc ggtgaagccg agcacgtcga aggtgcgcac      8700
gtcgttgcgg atcggctcgg cggagccggg gtcgaggagc tggtcgaggc gttcgcgggc     8760
gccgaccggg tggtgtttgg cgcattcggg gcagacccgc aggccgcggg cccagcgctt     8820
gccgtacacg gcgcgcggc agttgccgca ctgcacccag tcggcgacgc cggtcgtggg      8880
ccggatggcg gtttcggtca tgtcgttgtc tccctcggtt ctcagcccgc ggtctcgacg     8940
agcaggccgt tgacgaacgc gaccatgtcg cgcggtgtct ccaggccgtc gatgtcgtcg     9000
tcggagatgg cgacgccgcg ctcgtcctgg atccgggtga cgacctcgta gacggcgagc    9060
gagtcgaggc cgaggtccag gaacggggtg gccgcgccgg tctcgtcgag ctggaccgcg    9120
tcgtcggtgc cgacgcacgc gtcgatcagc cgcttgaggt cgtcgagcgt gaagggtcc     9180 atgggttcgt cctcccggtg gtctggcttc ctgccgaacg cagacagcca ctgtcggccg    9240
gccggatgga ggtctggtcg agagccgctg gatgtgcgcc ggagggcgcg gcgtcggctt    9300
cgagtcggct tccggcgggc ttcgagggg cgccgcgcat gctcggtgcg cgccctctc       9360 ccgccggacg ccgccggacg cccggcgggt cccagacggg gttcaggcgg gtgtcaggcg     9420
agaccagaac cgcgaaaggt ggtcgcgatg cccggacttc gggttcccga gcggcgtttc    9480
agccgtgttc tcggggtcgg ttcgtaccgg ccccgccgtg aggtgagcaa caaggaggtg   9540
tgcacctgga tcgactcgac ggaggagtgg atcgagacgc gcaccgggat caggtcgcgg     9600
cggatcgccg agccggacga gacgatccag gtgatggggg tggccgcgag ccgccgcgcg    9660
ctggagcacg ccggcgtgga tccggccgag atcgacctgg tcgtggtctc cacgatgacc     9720
aacttcgtgc acacgccgcc gctttcggtc gcgatcgcg acgagctggg tgccgacaac      9780
gccggcgggt tcgacctgtc ggcggcgtgc gcggggttct gccacgcgtt gtcgatcgcg    9840
gcggacgcgg tggagtccgg cggttcgcgg cacgtgctcg tggtggcgac ggagcggatg    9900
accgacgtga tcgacctggc ggaccggagc ctgtcgttcc tgttcggcga cggcgccggc    9960
```

| | |
|---|---|
| gcggccgtgg tcggcccgtc cgacgtgccc ggcatcggtc cggtggtgcg cggcatcgac | 10020 |
| ggcaccggcc tgggctcgct gcacatgagc agttcgtggg accagtacgt cgaggacccc | 10080 |
| tcggtgggcc ggccggcgct ggtgatggac ggcaagcggg tgttccgctg gcggtcgcg | 10140 |
| gacgtcgtcc cggcggcccg cgaggcgctc gaggtggccg gcctgaccgt cggggacctg | 10200 |
| gtggcgttcg tcccgcacca ggccaacctg cggatcatcg acgtgctggt ggaccggctc | 10260 |
| ggcgtgccgg agcacgtggt cgtctcgcgc gacgcggagg acaccggcaa cacctcgtcg | 10320 |
| gcgtcggtgg ccctggccct ggaccggctg gtgcgctccg gcgcggtgcc cggcggcggg | 10380 |
| cccgcgctga tgatcggttt cggcgccggg ctgagctacg cgggccaggc tctactgctt | 10440 |
| cccgacccgc cgtccactcc ggcttgagcg gcgttctagc cgccgcccgc aagctcggca | 10500 |
| tcaaccccag tcggccgcat cacccgtcaa ggagatccac cgtgatcgtg cacaccctga | 10560 |
| tctaccgttt cccggcctcc gtcccgcagg aggacctgga cgcgttcttc gacgcggcgc | 10620 |
| gcgagctggt gctgagcacc ggcctgatga acgcgttcga cgtcaagccg cacctgtggc | 10680 |
| tgcccgccga cgaccgcgcc cgcggcatga cggccggcta catcgtgcag ttcgtgtgcg | 10740 |
| acgacctgga cgcgctcgcg aagttctccg agctgcccac cgtctacgac ttcatcacgg | 10800 |
| actggaaggc ccgcctgcag ttcgaggcgg cgtacgccaa ccacgaggcg ctcgacctca | 10860 |
| cccccaccgc ctgagcccgc ccaaccaccg aggagcaccc tcatgcgtca cgtcgaacac | 10920 |
| accgtcaccg tagcgccccc ggccgacctg gtctgggagg tgctggccga tgtgctcggc | 10980 |
| tacgccgaca tcttcccgcc gaccgagaag gtcgagatcc tcgaggaggg tcaggctac | 11040 |
| caggtcgtcc gcctgcacgt ggacgtcgcc ggcgagatca acacctggac ctcgcgccgc | 11100 |
| gacctggacc cggcccgccg cgtcatcgcc taccggcagt ggagacggc cccgatcgtc | 11160 |
| gggcacatga gcggcgagtg gcgcgccttc acgctggacg ccgagcgcac ccaactggtg | 11220 |
| ctcacccacg acttcgtgac gcgcgcggcc ggcgacgacg gcctggtggc cggcaagctc | 11280 |
| accccgacg aggcgcgcga gatgctggag gcggtcgtcg agcgcaacag cgtcgccgac | 11340 |
| ctgaacgcgg tgctcggcga ggccgagcgt cgggtgcgcg cggccggcgg cgtcgggacg | 11400 |
| gtgaccgcgt gagcggccgc aagacgttcc tcgacctgag cttcgcgacc cgggacaccc | 11460 |
| ccagcgaggc caccccggtc gtcgtcgacc tgctcgacca cgtgaccggc gcgacggtgc | 11520 |
| tcgggctgag ccccgaggac ttccccgacg gcatggccat ctcgaacgag acggtcaccc | 11580 |
| tcaccacgca caccggcacg cacatggacg cgccgctgca ctacgcccg ctcagcggcg | 11640 |
| gcgtgccggc caagtcgatc gaccaggtcc cgctggagtg gtgctacggc ccgggcgtgc | 11700 |
| gcctggacgt gcggcacgtg ccggccgcg acggcatcac cgtcgaccac ctcaacgccg | 11760 |
| cgctcgacgc cgccgagcac gacctggcgc ccggcgacat cgtcatgttg tggaccggcg | 11820 |
| cggacgccct gtggggcacc cgcgagtacc tgtccacctt ccccgactg accggcaagg | 11880 |
| gaacgcagtt cctggtcgag gcgggcgtga aggtgatcgg catcgacgcg tggggcctgg | 11940 |
| accggccgat ggccgcgatg atcgaggagt accggcgtac cggcgacaag ggcgccttgt | 12000 |
| ggccggcgca cgtctacggg cgcacccgcg aatacctcca gttggagaag ctcaacaacc | 12060 |
| tgggcgcgct gccggcgcc accggatacg acatcagttg cttcccggtc gccgtcgcgg | 12120 |
| gcaccggtgc gggctggacc cgggtggtcg ccgtgttcga gcaggaagag gaggactagt | 12180 |
| ccatggacgc cgacgtcatc atcgccggtc ccggccccac cggactcatg ctggccgccg | 12240 |
| agctgcgggct ggcggcgcc gacgtgctga tcctggagct gctgccggag cccaccggcc | 12300 |
| agtcgcgcgc gctcggcatc aacccgcgcg ccgtcgaact gctggacgcg cgcggcctga | 12360 |

-continued

```
tgggccggtt cgccgaccag cacaccatca ccaactcgca ctacggcgcg ctgcaccgcc    12420
cgctggactt cagccggctc gacaccgcgc acggcgtcat gatggtgccg cagcgccgca    12480
ccgagaagga actgggcgag tgggcccggg ggttgggcgc acgaatactg cacgggcaca    12540
ccgtggtcgg actgacccag tacgccgacc gggtcgaggt cgaggccgac acgtccgagg    12600
gcacacgcac cttcaccgcg cggtacgtgg tcggcgccga cggcagccgc agcagtgtgc    12660
ggcagttgtc cggcatcggc tacccgggcg tgccgtcgac cgtcgacgcg ctcatgtgcg    12720
acgtgtcggg cctggacctg gccttcaagt tcttcgagcg caacgaccgt ggcttgtggg    12780
cggtgttccc ggtcggcgac ggcgtcttcc gggtcgtggt ctacgcgttc gaccgcccgc    12840
cggtgcgcgc cgcggacgcg ccctccttcg aggaggtcaa cgacgcggcc cgcaccattg    12900
cggggatcga cctgaccggc ggcacgccgc actggctgag ccggcacggc aacaccaccc    12960
ggatcgccga ccgttccgc gccgagcggg tgttcctggc cggcgacgcg cgcacgtgg     13020 tcccgccggc gggcggccag ttgctgacca ccgggctgca cgacgcgacc aacctgggct    13080
ggaagctcgg cgcggcggtc gccggctggg ggtccgacga cctgctcgac agctaccagg    13140
acgagcggta cccggtcgcc gagcggatca tcctcaacgc gcgcgtgcag aacctgctca    13200
tgtcgggcgg cctggacatc gccgcgctgc gcgaactgtt caccgagctg gtcgagttcg    13260
acgaggtgaa cttctacctg tcgggtcagc tcagcgcggt gtcggtgcgc tacgacgtcg    13320
gcggcgacca cccgatgctg ggcctggggc tgccgcaccg cacgctggag accgacgcgg    13380
gcgaggtgac caccaccgag ctgctgcggt cggcgcgcgg gctgcttctg gaggtcgggg    13440
acgcgcctgg cttcgcggac ctggtcgcgc cgtacgcgga ccgggtggac gtccgggtcg    13500
cgcgcgtccc ggccggctcc cccgggttcg acggggtcac cgccgtgctg gtccgcccgg    13560
acacgcacgt cgcgtgggtc gccgagaccc ccgcgggcgc cgacgcggcg gacgcggacc    13620
gcgacgcgct cggcaccgcg ctgcgccgct ggttcggcgc gccggccgac acgaactccg    13680
gcgcggaatc cggtacggag tccggcacgc agaccgccgc cccgtcggc gccgggaccg     13740 ccggggggcac gccatgaccc tcgacgacgg cgcggtcctc gcgcccgccg ccgtcctgac    13800
ggcggcgctg cgccgccggg agatctccag ccgcgaactg ctcgacctgt acctggcccg    13860
cgtcgaggcg gtgaacccgg cgctgaacgc cgtggtcacc ctcgacgtgg aacggcccg     13920 ccgcgaggcg gccgaggcgg accgcgcgac ggcggccggc gcccgtaccg ggccgctgca    13980
cgggctgccg atgacggtca aggacaccct ggagaccgag ggtctgcgca ccacggccgg    14040
cgccgcggaa ctggccgagc acgtgccggc ccgcgacgcg gactcggtgg cgctgctgcg    14100
ccgcgcgggc gcggtggtgt tcggcaagac caacaccgcc acctacgcct ccgacgcgca    14160
gacctacaac ccggtgttcg gcaccaccaa caacccgtgg gacacctccc gcgcgccggg    14220
cgggtcctcg gcggcgcgg cggccgcgct cgccgccggg ctgacgtcgc tggaactggg    14280
cggcgagctg tccggttcgg cgcgctaccc ggcgcactgc tgcggcgtgt tcgcgctgcg    14340
gccgtccttc gggatcgtgc cgatcgcgcg ccacatcccg cgccaaccgg ggtcgctgaa    14400
gaccaacgac atggtgacgc tggcgccgct cgcccgcagc gcggccgacc tcgacctgct    14460
gctcgacgtg ctgccccggc cggccgccga caaggcgccc cgctggcgcc tggacctgcc    14520
cgcgccgcgc gccgaatcgc tgggcgggct gcgcgtgggg ctgtggctgg acgacccgct    14580
gtgcccggtc gacgccgagg tcggcgacgt gctggcggcg gcggtcgacg ccctcaaggg    14640
caccggcgtc gcacggctgg cggacgtcac gccggtcgac cgcgcgacgc acgaccggct    14700
```

```
ctacgagcgg ctgttgcagg gcgcggtcag tctcggactg cccgcccggg tgtacgcggc    14760
caaccaggcc gcggccgccg cgctcgcccc cgacgacgac tcgccgcgcg cgtcgttcct    14820
gcgcgccgcg acgctgtcgc accgcgactg gctggcggcc gacgaggagc gcgagcacca    14880
gcgggcccgt tgggccgagg tgttcgacga gttcgacgtc gtcctgtcgc ccgtcgcgcc    14940
ggtcgtcgcg acgccgcacg accagcgtcc cgacctgtcc gcgcggcgga tcaccgtcaa    15000
cggcgcccaa cggccctact gggacatcat ccgctggacc agcccggcca ccgcggccgg    15060
cctgccggcc gcgtccgtcc cggtgggggt gcccgttcg gcctgccgg tcgggctcca     15120 ggtggtcggc ccgcacctgc acgaccgcac cgtcacgtgg ttcgcccggc gtgtctcgga    15180
gctgctcggc ggcttccagg ccccgcccct gcgcgccgcc gggaacgacg gggcgtcccc    15240
cggatcatca cgaacggaag gagcggaccg tgcctgagtc cgacggcatc gacggcacct    15300
accccgtcgt catcgcgggc ggcggccgg tcggcaccat gctggcgtgc gggctgcggc     15360
aggccggcgt cgacgttctg gtgctcgaac gccgcaccga gcccgacctg ttgccgcgcg    15420
ccggctcgat gggcccgctg gcgttcgagg cgctggaacg gctcggcctg cacgacgcgc    15480
tgctggccgc cgagcaggac acgctcgccg agtacgcaa gatgttcgcc gactgggcgg     15540
ccaagaaggg catcgccag ccggccaccc gctccgcgcc caaggagcac ttcgcgggcc     15600
tggagaagat cgacccggcc cgccgcaccg accccgagcc ccgccgggtg cgcgtcgagc    15660
agccggtgct cgaggagatc ctgcaccggc acgcggtgtc gctcggcgcg gtgatcctgc    15720
gcggccacga gatcgtcggc gtgttccagg acgaggagcg cgtcatcgtc gacgtgcgca    15780
ccgtcgacgg gaccgtcgcc caggtgacca cgcagtacct ggtcggcgcc gacggcgcgg    15840
acagcagcgt gcgcggcttc gtcggcttcg acttccccgg caccgacgcg accgtcaccg    15900
gccgcatggc ggtcgtggag ttggccgacg aggagaaact ctccccgggc ttccactaca    15960
cgccggtcgg cctgtacgtg cacggcctgg gcgtcaaccg gctgtcgacg gtcgagttcg    16020
acggtccgcc gaccgacgac gaggacatga ccgccgagga gctgcagggc agcatccgac    16080
gggtcagcgg cacggacgtg acgatcagcg agatgtcctc gggcacccgc tggatcgaca    16140
cggcgcggca ggcgtccgcg taccggctcg gccgggtgct gctggccggc gacgcggcgc    16200
acgtgtacgc gccggtcggc ggccagggcc tcaacgtcgg cctggtcgac gcggccaacc    16260
tcgtgtggaa gctggccgcg caggtacagc gctgggcgcc gcactatctc ctcgacacct    16320
acggttcgga gcgctacccg gtcgccgcgc ggctgttgca gaacacccgc gcgcagatcg    16380
cgctcatgca ccccgacccg cagaccaccg cgctgcgcga gatgttcgag gaactgctcg    16440
acatcgacga ggtgcaccgc acgatcgccg acatgatggc cggaatggac gtgcggtacg    16500
ccgtcgaggg cgagcatccg ctcctcggca cgctggtccc ggacgccaag ctcaccggcg    16560
gcaaggccgc cgacctgtgg gcggacgggc cggcgtgct cgtcgacttc gccgaccgcg     16620
cggacgtgcg cgacgcggtc ggcgcgtggt cggcgcgggt caacgtcgtc acgttgcccg    16680
gcgcgcgcga ggacgtcgac gcgctgctgg tccggcccga cggctgcgtg gtgtgggcgc    16740
tgcccaccgg cgcggcgctc gccgacgcgc ccccgaccga ggccctgacc acgtggttcg    16800
gacgcgcccc gcgcgtgtcc tgagcaatcc caccccatcg cgaaggagat tccgaacacc    16860
atgacgatcg acgacctgcg caggatcctg accgagtgcg ccggcgagga cgagtccgtc    16920
gacctgggcg gcgacatcct ggacacgccg ttcaccgagc tgggctacga ctcgctcgcg    16980
ctgatggaga ccgccgcccg catcgagcag gagttcggtg tcgcgatacc ggacgacgag    17040
ttcgccgaac tggcgacgcc gcgtgcggtg ttggccgcgg tctccacggc ggtctcggcc    17100
```

```
gcggcctgag ccgcggcccg gccccgggt tccgaggcgc ggtgcttgcg gtgcccgcgc   17160
tgccgcggtg ccgcagcccg gttccgcggc cggaatccgg ccaccgtctc ccgtgtcccg   17220
cccccatcgg ctcaggggcg ggacacggt gtgttccgcg ccgcgactcg cccccgagcg   17280
tgccggtgtg aggtaatcgt cccgggaaag ggaaggcgtc gccatgtcgc tcggtcgggt   17340
gctcgtcgtc gacgacgaac ccaagatccg catgatcgtc cggggttacc tcgaggccga   17400
cggctacaag gtcgtcgagg cgtgccacgg tcgcnaccgg cccgacttgt tccgacggc   17460 ctgcgcgcca tcgtgcgcga ccggcccgac ctggtcgtcc tggacgtgat gttgcccggc   17520
ctggacggct tcgaggtgct gcgccggttg cgcgccaccg tcgaccggac cccggtcatc   17580
ctgctgaccg cgcgcgccga ggaggtggac cgggtcatcg ggttcaccgc cggcggcgac   17640
gactacgtca ccaagccctt cagcgcccgc gaactcgcct tgcgggtccg cgcggtgctg   17700
cgccgctgcc agccggacga gcgggccgcc gagcccgacg acacgctgcg cttcgccgac   17760
atcgagatcg acccgaccgc gcgggtcgtc accgtcgacg gcgcccccgt cgggccgctg   17820
accgcactgg acttcgacct gctgctcgca ctcgcccgcg cgcccggacg cgtcttcacc   17880
cgccaccggc tcctcgaaca cgtctgggcg ccgcgacgcgt tcggcgacga ccgggtggtg   17940
gacgtgcacg tgcgcacact gcgccgcgcg ctcggggacg acgccgccgc gccgcgattc   18000
gtcgggacgg tgcgcgcggt cggctaccgg ttcctggccg gcgccgccgc ccacgcctga   18060
gccggcgagt gtgagactcg ggcgagcccc gcttcacaca gcttcacgg agcgcaccgc   18120 cgtcgtcaca cgaactcccg gtgtgctgga ggcatgacaa ccaccgaagc ggcacctccc   18180
cccgcagcgt ccacgcgcgt ggccgcctcc gtcgtcgccg cgtcaagtc ctacggttcg   18240 ggcgacgacg agatccgcgc gctcgacggc gtgaccatag agttcgcctc cggcgagttc   18300
accgccgtca tgggcccctc cggctcgggc aagtcgaccc tgatgcactg cgcggcgggc   18360
ctggaccggc tcacctcggg ccacgcgtcg cgtacatcgg cgacaccgac ctcggcaccc   18420
tgccggaccg cgagttgacg ttgctgcgcc gcagccgggt cggcttcgtc ttccaggcgt   18480
acaacctcat ctccacgctc aacgcgcggg agaacatcct gctgccgcag aacctcgccg   18540
gcgtgcgccc ggacctggag ttcctgggcg aggtggtgga ccggctcggg ctcggcgcgc   18600
gtctgcggca ccgccccggc gagttgtccg gcgggcagca gcagcgggtc gcggtggcgc   18660
gcgccctggt cagcaggccg gacatcgtct tcgccgacga gccgaccggc aacctggaca   18720
gcgccgcgag caccgaggtg ctggagttcc tgcgcggcac cgcgaacgag ctgtgccaga   18780
ccatcgtgat ggtcacccac gacccgcaca ccgccgccta cgccgaccgc gcggtgttcc   18840
tcgccgacgg ccgggtcgtc gacagcatcg ccgcccccac cgccgaagcg gtcctggagc   18900
gtatgaaggg cttccgaagg tgaacggttt ggtgcgcgcc gcgctcgccg gtgtgtgggt   18960
gcgccgcgct cggtatgcga tgaccgtcgc ggcggtcgtc ctgtcggtca tgttcatgac   19020 cgccacctc atgctcacca gcggtctggg cgaccgcgag aaggaccaga tcacccgggc   19080
cggcgccggc gtcgacgcgg tggtgcgcgg cccggtggtc gccgacccgg agggcgggcc   19140
cggcgaggtg cagacgcccg cgcgggtgcc ggtcgacgac gcggtgctcg cggcggtacg   19200
ggcgaccccc ggcgtgagcg cggcggccgg cagcgtcaac ggctatgcgc gcctggcccg   19260
ttccgggtcg cggctgctcg gtttcgagga cgccaccgc gacgtgggct cggcgtggat   19320
cgacgacgac gcgctgaatc cgtatcggct cgccgagggc cacgcgccgc acggcgcggg   19380
cgaggtcgtc gtggacgcgg ccgccgcgcg ccgcgaccac atctccgtcg gcgaacggtt   19440
```

-continued

```
gtcgctgctg accccgagcg ggcgcggcga cgtgacggtc gtgggcgtgg cccgctacgt   19500
cggcgacgat gggccggcgg acaagagcgc tgtgctgctc gacgcggccg tcgcgcccgg   19560
cctgttcggg cacgcgggcg gctacgaggc catcctggtg cgcggcgccg gcgggcacga   19620
cgcggcggca cgcgaggcat tggcgacctc ggtgggcgg acggtcgcgg ccgtgccgcg   19680
cgccgggccg gtgccggcac cgggcgcggt cgccgggccg gtgtggacgg gcgagctgcg   19740
cgacgcggtc ggcaccgcgt acgacaccct cacgatcatc ctggacggcg cggcgttcat   19800
cgcgctgctg gtcggcgccg cgctggtgca caacacgttc accgccgtca ccgcgcaacg   19860
gctgcgcgaa ctggcgctga tgcgggcact gggcgccacc cggcggcagg tcaccgcgtc   19920
ggtgctggcc gaggcggcgg tggtcggcgc ggtggccggc gtgctcggga tagcgctggg   19980
cgcgctcgcc gcgcggatcc ggcgcatgcg cttggcgatc tgctcgactt cggtgacctg   20040
ggcccgttcg aagatcaggt tgagcagccg gtctttcatc ggttgcctcc tcgtgacgaa   20100
gggaaacggg agccccgggt agggccgggg cttccgtgct caccggacgg gcggtccgcc   20160
aaccgcgccg tccgtcggcc ggagtcaccc gaccagttgg tactcgcggc cttccagcgc   20220
gggatcggcg tcgaggatcg cgcgctgcaa ctggtgcagc cacggcgacg gttcgaggcc   20280
gagctcgtcg agcatcgtca ggcgcagccg ctggaacacg tccagcgcgt gggtgcgcct   20340
gccgcaccgg tacagggcca gcatgagctg gccgtgcagg ccctcgtgcg tccggtcgag   20400
cgcggcgagc ccggacagct cgtccacgat cgtgtagtgc cggccgagcg cgaggtcgat   20460
ctggatgcga cggtcgacca ccgcgcgacg ccggccttcg aggcggagga tctccgcttc   20520
gaggaccggg ccgacgtgca cgtcgaccaa ggcggggccg cgccacagcg cgacggcctg   20580
ccgtaagagt tccgaggagg tgcggtagtc gccctcctcg cacttgcgca tgcccaggtt   20640
cgcgaggcgg tcgaactcga ccacgtccga catgccgtcc gggctggcca acaggtagcc   20700
ggtcccacac gtcatgatga tttccttggc gcgcgccttg gagttctccg ccgacgttcc   20760
cgcgaccagt cgcttcgcga tacggttccg gatatgcaga atataagtct gcaacgtcgt   20820
cgaagcgctc ttgggaaggt ccacgggcca cagctcgtct cggattctcc gagtcgtgac   20880
cacgttgttc gaattgactg ccagcagcgt cagaaggcta cgcggcttgg gggcgctcgg   20940
gacgacggtc aagccgtcca gatcgacctg cagcggtccc agtatgccga tatccaccat   21000 catccccga tgtgaataca tccttggagc ggctgtcatt gggttttga cctgcgattt   21060 tgtggacggt aattcccctc ttcccctccc ttgcggagca cttttccggta ccgtcgcacg   21120 cgggtcgcca tcccgatctc ggacactatc acccggtgcg gaactgccgt gttgccggaa   21180
cgtaaaaatg gctgccaata ggacggttgg tgcactgccg ggctcattcg cgacggtccg   21240
acgaccggaa atggcggtta tcagggcagc agaaacgacc cgccagtgtg cgggtctgga   21300
atattctgtt ctggagggtc ctgcgggaac tccgtcgaaa tcggaggga aaaccctcag   21360 gaatcgacgg gggtcgcggt cagaccgttg atcaggacgt tgaccgcgaa atcgaagcgt   21420
tgttccgcgg tgccgtaggt caggtgttcc gagagtgccg ccaggtcgg atagcggccg   21480 gactccaggg cgtcgaggac gtcgacgatg cccgaggcgc gccggcgctc ggactgcgcc   21540
tcgtccaact ggtggtcggt cccgcccggg cttccgttcg aacccgccgc gccggccggg   21600
gcgccggtcg tcgggtcggc gggtcgggcg acgccttcca ggctggcctc gtacgcgacc   21660
gccgaggtgt agaggccgag caggtcgcac gcccacgccg cggtctgcgc cgagacgccg   21720
ccggccagca gcagcgccgt ggtgcgttcc gcgatcgcga tggacgccgg gccggtgggg   21780
atgcggccca tcgagacctg ggcgatgccc gggtgcgcgt tcatggcagc caccgtcaag   21840
```

```
cgcagcagtt cgaccaactg gctgcgccag cgcgccggtt cgatcgggtc gaggggaacc  21900
gtcgacaaca ccgcgtcgag cgcctggcgc agcaggtcgt cgcggttgtc gacgtagacg  21960
tacaacgacg ccggtccggt gtcgagctcg ttggcgaccc ggcgcatggt gaccgacgag  22020
agtccttcgc tctgcaggat gcgcagagct gtctcgacga ccacctcctg gctgaggggc  22080
gccttggcgg ggcgggctct ggtactgcgc gaagtgacgg ccatgcggcg agtgtagcag  22140
ttgacacgaa tgttgttcgt gacagacgat gttcgtaacg aacaacgttc gttacgaaca  22200
gcgtttgccg ctctcgggcc cctgtccggc ccactcttcc gccaaggaaa cgccatggat  22260
tccaacccga tcacccttcc cgcgaacgga ccggtggccg aaccattggg cgagtcgccg  22320
gccgagccac ccggcaccgg accggcgccg tacgcggctc gctggatggt cctcgccgtc  22380
gtcttggtcg ccgaggtcat ggacctgctc gacgcgacca tcaccagcgt cgccgcaccg  22440
tcgatgtcgg cgccgcgtac accctgccgt tcgccgtctt cctcatcacc gccggccgac  22500
tcggcgacat ctggggccgg cgccggctct tcgtcatcgg cgcgggcggc ttcacgatcg  22560
cgtccgcgtt gtgcgcgctg gcgaactcgc cggaaatgct gatcaccacc cgcgcgctgc  22620
agggcgcgct cggcgcgctg ctcatcccgc agggcttcgg gctgatcaag gaggtcttcc  22680
cggacaagga actgggcaag gcgttcgcgc tgttcggccc ggtcatgggc ctgtcggcgg  22740
tgctcggccc gatcatcggc ggcgcgctgg tggacggcga cctgttcggc accggctggc  22800
ggatgatctt cctgatcaac ctgccgctcg gtgtcctcgc cgtactcggc gcgttccgct  22860
acatgccgac cggcgcgcgg atccggtgtg ctcaacgccg tccagcagtt cgccaacgcg  22920
atcggcgtcg cggtcgtcgc gacgatcttc ttcgcctacc tcgagacggc cacacctcct  22980
ccgaggcgat gacccgcacc gccgtcgcca cctgcgggct gctcgcgctg gcgttcctcg  23040
ccggcttcgc gctgccgcgc acggcacggg aagaaggcca ctagccggcc gccccggccg  23100
cgtcgtcgcg gccacacggt ggccgcaccc tggccacacc cctggaaaag ccggtcggac  23160
cgggcacgca ccggcggcac tcgcggtgcg tcacgtcccc ggtccggccg gcccggccga  23220
ccgccctcgg ccctcaagcg cggtcccctc cgtgaccgtg accggtgacg cgcctcgcgt  23280
cccacctccg ccgccactcc ggcccgtccg ccccgggcat caccgcaccg acgaacgcgc  23340
caggagcaca tcacgtgtcc acgcaccgca ccccgagcc cgaacgcgcg gccgagcacc  23400
gcgaccgcga acgccttcgg ggccacgatc gagaccgaga ccgcgaccga gaccggatgc  23460
cacgccggat cggcgcgggt ttcgcgcgtg gtccccacgt ccacaccacg cacgtcctga  23520
agaccgagca gatcctcgac gtcgccgccg cgcacttcgg tgtcgagccg cccgagtgcc  23580
ggctcgtcga cgaggccgtc gaacacaccg ggaaacgcct cgcgttgaag gaggtgtacg  23640
cgatctggga ctagggtccg gattttttct aga                              23673
```

NON-STEROIDAL ESTROGEN-RECEPTOR ANTAGONISTS

This application claims benefit of Provisional Ser. Nos. 60/243,458 filed Oct. 25, 2000 and 60/179,305 filed Jan. 31, 2000.

This invention was made in part using United States government funding through the National Institute of Health Grant No. CA 77248.

FIELD OF THE INVENTION

This invention relates generally to non-steroidal estrogen-receptor (ER) antagonists that are useful as therapeutics in the treatment of advanced stage breast cancer. More particularly, this invention relates to the cloning and heterologous expression of genes encoding ER antagonists. This invention also relates to the use of such expression to overproduce the ER antagonist and analogs thereof.

BACKGROUND OF THE INVENTION

Non-steroidal estrogen-receptor (ER) antagonists are useful in the treatment of advanced stage breast cancer. One class of ER antagonists that has been shown to be particularly useful are the R1128 substances (Y. Hori et al., The Journal of Antibiotics, 46(7): 1055–1062.) These substances are anthraquinone natural products with in vitro and in vivo potency approaching that of Tamoxifen. However, many of these types of ER antagonists exhibit variable effects in different target tissue. For example, tamoxifen acts as an ER antagonist in breast tissue, but an ER agonist in bone (Love, R. R. et al., New England Journal of Medicine 26: 852–856 (1992)) and uterine tissue (Kedar, R. P. et al., Lancet 28: 1318–1321 (1992)). Likewise, Raloxifene is an ER antagonist in breast tissue and an ER agonist in bone but not in uterine tissue (Black, L., et al., J. Clin. Invest. 93: 63–69 (1994)).

Estrogen receptors are transcription factors that bind to estrogen response elements in the promoter region of certain estrogen-related genes. Thus, estrogen-like ligands are useful to modulate transcription of these genes (Katzenellenbogen, J. A. and Katzenellenbogen B. S. (1996) Chem. Biol. 3: 529–536.) Recent studies have suggested that the tissue-dependent variability exhibited by these ligands may be due to differential ligand binding and/or activation of the two ER subtypes, ER-α and ER-β, which each have different tissue expression patterns and ligand binding characteristics (Mosselman, S. et al. (1996) FEBS Letters 392: 49–53.) It has also been reported that the ligand-bound ERs may modulate transcription activation by binding to different types of DNA enhancer elements, such as the AP1 transcription factors (Paech, K. et al. (1997) Science 277: 1508–1510).

Accordingly, there is thus a significant need for new ER antagonists which can inhibit ER function in a predictable way at both ER-dependent and AP 1-dependent DNA binding sites.

SUMMARY OF THE INVENTION

The present invention includes the estrogen receptor antagonist shown in FIG. 3. Other aspects of the invention are found throughout the specification.

DETAILED DESCRIPTION OF THE INVENTION

Figure 1A:
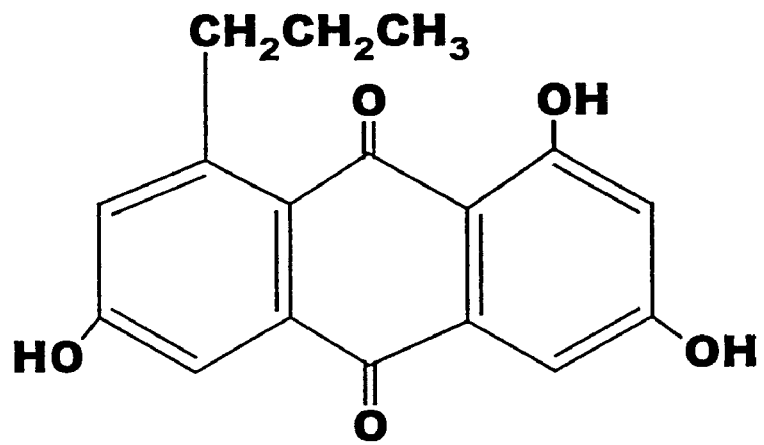
FIG. 1 depicts the structure of the R1128 compounds A (FIG. 1A), B (FIG. 1B), C (FIG. 1C) and D (FIG. 1D).
Figure 1B:
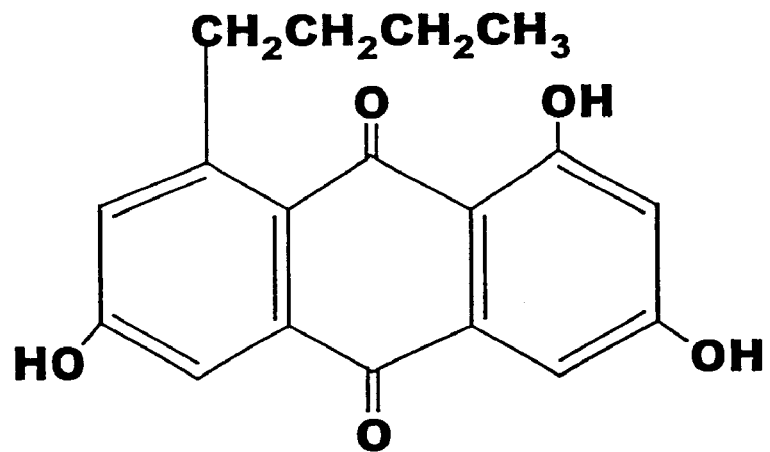

The present invention relates to the cloning and expression of the R1128 gene cluster in a manner that favors production of alternatively cyclized derivatives of the R1128 anthraquinones.

The isolation, fermentation, structures and properties of R1128 A–D (shown in FIGS. 1A to D) were described in 1993. See Hori, Y. et al. (1993) J. Antibiot. 46: 1055–1062 (Part I); 1063–1068 (Part II); and 1069–1075 (Part III). In Part II, the authors compared their pharmacological properties to tamoxifen, the non-steroidal estrogen-receptor antagonist that is a leading choice for treatment of advanced breast cancer. These molecules, which were identified as potent ER antagonists, had $IC_{50}$ values in the range of 0.1–0.3 mM. Although these activities were approximately 7–17 fold less than that of tamoxifen, their selectivity (50-fold better binding to ER as compared to the androgen receptor) and low toxicity (significant inhibition of tumor volume in a subrenal capsule assay at 100 mg/kg; no acute toxicity in mice or rats at 500 mg/kg) profiles were promising. (Yori, H. et al., supra, Part III.) Accordingly, it appears that manipulating the structures of natural tamoxifen-like products offers an opportunity to optimize their pharmacological properties.

In order to further study the pharmacological properties of R1128 as a first step towards engineering the structure to enhance its pharmacological properties, the present invention provides for a cloning procedure that allows the capture of the entire R1128 biosynthetic gene cluster and its expression in a model heterologous host, *Streptomyces lividans* K4-114 (Ziermann, R., et al. (1999) BioTechniquies 20: 106–110. Although described herein as an exemplary cloning procedure, it should be understood by one of skill in the art that other known cloning procedures and hosts can also be utilized to clone the compounds describe herein using routine cloning and expression optimization methodologies.

Recent studies on bacterial aromatic polyketide biosynthesis have demonstrated considerable promise with respect to altering four aspects of product structure: primer unit incorporation, chain length, degree and regiochemistry of reduction, and regiochemistry of cyclization. (R. McDaniel, et al., Nature 375: 549–554 (1995); and L. Han, et al., J. Bacteriol. 180:4481–4486 (1988).) Most of these features are potentially attractive targets for manipulation in the R1128 family of ER antagonists. For example, the incorporation of an additional ketide unit in the polyketide backbone could lead to the introduction of an aliphatic ketone functionality in place of the variable alkyl group. Likewise, elimination of the C-9 hydroxyl has been accomplished in similar systems by co-expression of a suitable ketoreductase with regiospecificfty towards the C-9 carbonyl of the nascent polyketide backbone. Finally, of particular interest is the variable functional group in the R1128 anthraquinone series, which is presumably derived from alternative primer unit incorporation in the polyketide backbone. The recent identification of a single protein as the principal determinant of primer unit specificity in bacterial aromatic polyketide biosynthesis suggests that it should also be possible to predictively alter this functionality in the natural product.

A minimal prerequisite for biosynthetic engineering of natural products is the availability of cloned genes, which are typically clustered and coordinately regulated in microorganisms. An ideal strategy for cloning a desired gene cluster would involve its direct identification through heterologous expression in a biologically friendly host. Building on the pioneering studies of Hopwood and coworkers (Malpartida, F. et al. (1984) Nature 309: 462–464), recent studies have successfully demonstrated the ability of an organism, such as *S. lividans*, to produce heterologous aromatic polyketides (Hong, S. T., et al. (1997) J. Bacteriol. 179: 470–476; and Gould, S. J., et al. (1998) 51: 52–57.) However, due to the limitations of the integrative vectors used in such efforts, genomic libraries had to be pre-screened for candidate cosmids carrying putative polyketide genes prior to their transfer into *S. lividans*.

Accordingly, other vector systems capable of exhibiting a larger DNA carrying capacity for DNA are more preferred for use in the present invention. The pHU204 vector, which is a 12.16 kb derivative of pRM5, has such properties (McDaniel, R., et al. (1993) Science 262: 1546–1550.) Among other features, it has the well-characterized SCP2* replicon. While its carrying capacity as a cosmid cloning vector in *E. coli* is limited to 40 kb inserts, SCP2* vectors have been used to clone significantly larger fragments in *S. lividans*.

The organization of the R1128 gene cluster is shown below in Table I and the sequence is given below in Seq. ID No. 1

EXAMPLES

Example 1

Cloning of the R1128 Gene Cluster

Figure 1C:
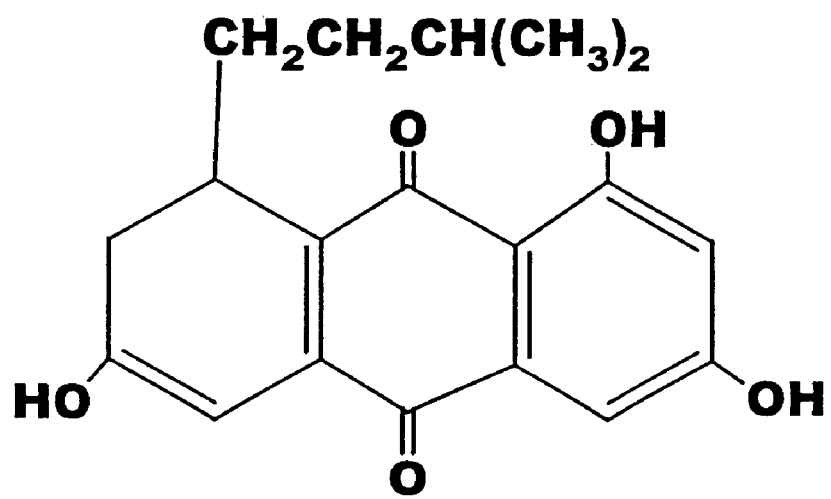
Figure 1D:
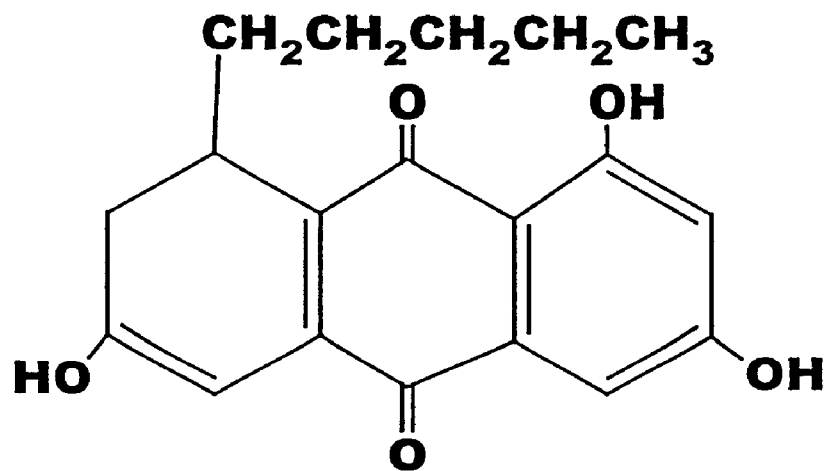
Figure 2:
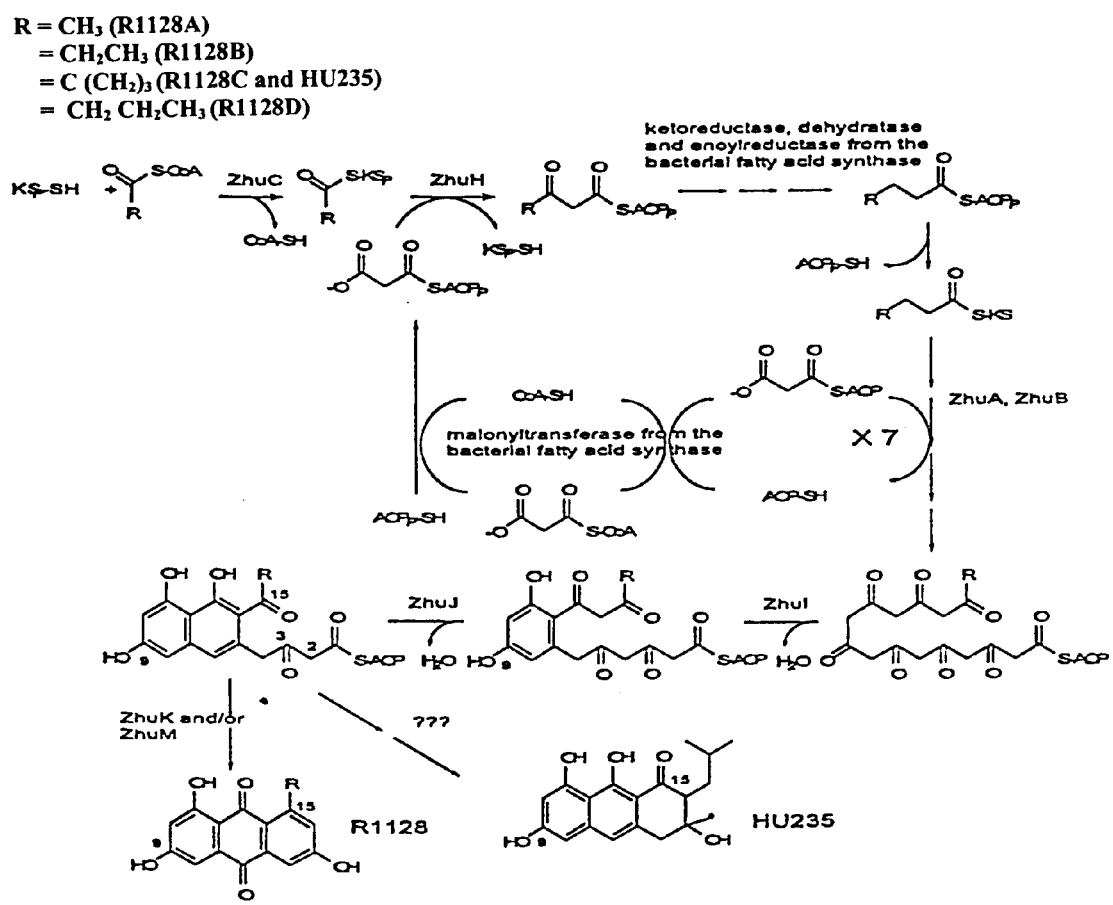
FIG. 2 depicts the biosynthetic pathway leading to the R1128 compounds A–D.

Anticipating that the R1128 gene cluster was under 40 kb in size, a cosmid library was constructed in pHU204 (McDaniel, R., et al. (1993) Science 262: 1546–1550) using genomic DNA derived from *Streptomyces sp.* R1128, the R1128 producer. The entire library was transformed without prior screening into *S. lividans* K4-114. Several pigmented colonies were identified; one of them, which was designated K4-114/pHU235, was cultivated on a larger scale (500 mL on semi-solid R5 agar medium). After neutral extraction and pre-purification using column chromatography, two major UV-active peaks were collected from reversed-phase HPLC, dried, and analyzed. Mass-, 1H and 13C NMR spectra revealed that one of the compounds was identical to R1128C (FIG. 1C). The purified yield of the compound was 0.5 mg/L. The second compound, designated HU235 (FIG. 2), was produced in considerably greater quantifies (16 mg/L), and was structurally characterized by 1H, 13C, 1H, 1H-COSY, HMBC, HMQC, ROESY-NMR, and IR spectroscopy. Mass spectrometry was performed with the acetylated derivatives 6 and 7. The polyketide origin of HU235 was established by feeding of 1,2-13C sodium acetate, which gave the expected incorporation pattern as observed

TABLE I

Organization of the R1128 Gene Cluster

| Gene No. | Gene Function | Start | Stop | Length (bp) | Length AA | Start Codon | Stop Codon |
|---|---|---|---|---|---|---|---|
| | | | | 0 | | | |
| 1 | Chain Length factor | 1623 | 376 | 1248 | 416 | ATG | TAG |
| 2 | ketosynthase | 2873 | 1620 | 1254 | 418 | ATG | TGA |
| 3 | Acyltransferase | 3067 | 4113 | 1047 | 349 | ATG | TGA |
| 4 | Acetyl-CoA carboxylase subunit 3 (Biotin carboxylase) | 6207 | 4822 | 1386 | 462 | ATG | TGA |
| 5 | Acetyl-CoA carboxylase subunit 2 (Biotin carrier protein) | 6651 | 6214 | 438 | 146 | ATG | TAG |
| 6 | Acetyl-CoA carboxylase subunit 1 | 8901 | 7165 | 1737 | 579 | ATG | TGA |
| 7 | Acyl Carrier Protein 1 | 9182 | 8922 | 261 | 87 | ATG | TGA |
| 8 | Priming ketosynthase | 9448 | 10467 | 1020 | 340 | ATG | TGA |
| 9 | Aromatase/Cyclase | 10903 | 11412 | 510 | 170 | ATG | TGA |
| 10 | Cyclase 2 | 11409 | 12179 | 771 | 257 | GTG | TAG |
| 11 | Oxygenase 1 | 12183 | 13757 | 1575 | 525 | ATG | ? |
| 12 | Amidase | 13754 | 15277 | 1524 | 508 | ATG | TGA |
| 13 | Oxygenase 2 | 15270 | 16823 | 1554 | 518 | GTG | TGA |
| 14 | Acyl Carrier Protein 2 | 16861 | 17109 | 249 | 83 | ATG | TGA |
| 15 | Transcriptional regulator (has a 1 bp frameshift) | 17249 | 18060 | 812 | 271 | GTG | TGA |
| 16 | Transporter (has a 1 bp frameshift) | 18154 | 18923 | 770 | 257 | ATG | TGA |
| 17 | Oxygenase/Transporter | 18920 | 20122 | 1203 | 401 | GTG | TAG |
| 18 | Activator | 21003 | 20185 | 819 | 273 | ATG | TGA |
| 19 | Repressor | 22124 | 21357 | 768 | 256 | ATG | TGA |
| 20 | Activator | 22255 | 22992 | 738 | 246 | ATG | TGA |

Figure 3:
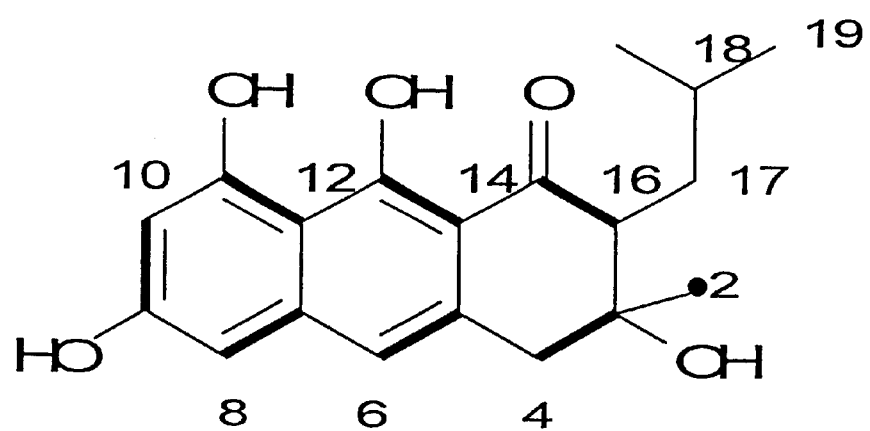
FIG. 3 depicts the product, HU235.

When this gene cluster was isolated and expressed as described in Example I, an alternatively cyclized, optically active product designated HU 235 (FIG. 2) was also produced. Because a mutation in the cloned gene structure abolishes production of HU 235, but still allows for production of R1128B and C, this suggests that the bioactive natural products might actually be side products, rather than the principal products, of the biosynthetic pathway shown in FIG. 3.

in the 13C NMR spectrum. It was initially suspected that HU235 was a shunt product resulting from low activity of a late-stage enzyme in the R1128 pathway. However, optical rotation analysis revealed that the compound HU235 was optically active ([a]D=33.0°), suggesting that it arose from stereocontrolled cyclization of a common biosynthetic intermediate (FIG. 1a). To test this hypothesis, we subjected cosmid pHU235 to in vitro transposon mutagenesis (R. McDaniel, et al., Nature 375: 549–554 (1995). Transformation of the resulting pool of mutagenized cosmids into *S. lividans* led to the identification of one clone, Tn164, that produced both R1128B and R1128C in 1.4 mg/L and 1.6 mg/L, respectively, while completely abolishing HU235 production. The result confirms that one or more enzymes encoded within the biosynthetic gene cluster are involved in the final stages of HU235 biosynthesis. If so, then the biologically active R1128 metabolites are probably side products of a biosynthetic pathway whose principal product is HU2353

Example 2

Isolation and Characterization of Products

To further study the products obtained in Example 1, the cultures were extracted with EtOAc. The extract was dried with MgSO4, evaporated, and subjected to column chromatography (SiO2, Hexane/EtOAc 1:1). The yellow fractions were dried and further separated on a preparative reverse phase HPLC column (25×150 mm, C18-IP column, Beckman, isocratic run with H2O (1% HOAc)/MeCN 55:45, flow 20 ml/min, UV-detection at I=250 and 350 nm. Three major UV-active peaks (tR=10.2, 22.5, and 28.3 min) were collected, dried, and analyzed. Spectral data of HU235 (5): [a]D (in CH3OH, c=0.63)+33.0°; 1H NMR (500 MHz, (CD$_3$)2SO): d=16.10 (s, 1 H-O-C(13)), 10.23 (s, 1 H-O-C (9)), 9.81 (s, 1 H-O-C(11)), 4.84 (s, 1 H-O-C(3)), 2.95 (2 d, J=16.3, 2 H-C(4)), 2.58 (dd, J=8.1, 3.0, 1 H-C(16)), 1.75 (m, 1 H-C(2')), 1.64 (m, 1 H-C(1')), 1.57 (m, 1 H-C(1')), 1.25 (s, 3 H-C(2)), 0.95 (d, J=6.4, 3 H-C(3')), 0.91 (d, J=6.6, 3 H-C(3')). 13C NMR (125 MHz, (CD3)2SO, (coupling constants of 13C-enriched material, 100 MHz, (CD3)2SO)): d=206.4 (C(15), J (C,C)=39.9), 165.3 (C(13), J (C,C)=63.0), 161.3 (C(9), J (C,C)=65.0), 159.1 (C(11) J (C,C)=62.5), 140.8 (C(7), J (C,C)=58.2), 136.2 (C(5), J (C,C)=64.9), 115.9 (C(6), J (C,C)=64.9), 106.9 (C(14), J (C,C)=63.0), 106.4 (C(12)), J (C,C)=62.5), 101.7 (C(8), J (C,C)=58.2), 101.1 (C(10), J (C,C)=65.0), 71.2 (C(3), J (C,C)=36.8), 55.1 (C(16), J (C,C)=39.9), 41.2 (C(4), J (C,C)=36.8), 34.4 (C(1')), 28.0 (C(2)), 26.5 (C(2')), 22.5 (C(3')), 21.8 (C(3')); IR (KBr):~=3448m, 2956m, 2553w, 1638s, 1597s, 1458w, 1420w, 1384w, 1163m, 1095w, 917m, 848m. Acetylation of HU235: HU235 (5 mg) was stirred in 1 ml pyridine/Ac2O (3:2) for 2 h, the mixture was poured into 2 N HCl and extracted with ether. Two products were isolated after chromatographic separation (hexane-EtOAc 3:2). HU235Ac2 (6): 1H NMR (400 MHz, CDC13): d=7.33 (d, J=2.1, 1 H), 7.02 (s, 1 H), 6.87 (d, J=2.1, 1 H 3.21 (d, J=16.5, 1 H), 3.00 (d, J=16.5, 1 H), 2.60 (dd, J=8.3, 4.0, 1 H), 2.38 (s, 3 H), 2.33 (s, 3 H), 1.78 (m, 1 H), 1.66–1.53 (2 m, 2 H), 1.37 (s, 3 H), 0.99 (d, J=6.4, 3 H), 0.93 (d, J=6.5, 3 H); MS (FAB+): m/z (%): 459 (15) [M-H+2 Na+], 437 (100) [M+Na+]; 415 (20) [MH+]; HRMS (FAB+) calcd. for C23H26O7 Na+437.1576, found 437.1589. HU235Ac3 (7): 1H-NMR (400 MHz, CDCl3): d=7.57 and 7.55 (2 s, 1 H), 7.48 and 7.45 (2 d, J=2.1, 1 H), 6.95 and 6.93 (2 d, J=2.1, 1 H), 3.31 (m, 1 H), 3.15 (m, 1 H), 2.58 (m, 1 H), 2.47 and 2.45 (2 s, 3 H), 2.40 and 2.38 (2 s, 3 H), 2.33 and 2.31 (2 d, 3 H), 1.65–1.51, 1.78 (m, 1 H), 1.66–1.53, 1.42–1.34 (2 m, 3 H), 1.36 and 1.34 (2 s, 3 H), 0.96–0.84 (m, 6 H); MS (FAB+): m/z (%): 479 (100) [M+Na+]; HRMS (FAB+): calcd. for C25H28O8 Na+479.1682, found 479.1695.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

We claim:
1. An estrogen receptor antagonist given by the formula:

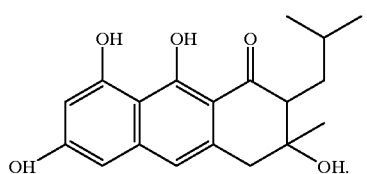

* * * * *